United States Patent [19]

Gracen et al.

[11] Patent Number: 4,569,152

[45] Date of Patent: Feb. 11, 1986

[54] LBN CYTOPLASM

[75] Inventors: Vernon E. Gracen, Ithaca, N.Y.; Paul Sisco, Cary, N.C.; Pierre Bouthyette, Ithaca, N.Y.

[73] Assignees: Agrigenetics Research Associates Limited, Boulder, Colo.; Cornell Research Foundation, Ithaca, N.Y.

[21] Appl. No.: 604,148

[22] Filed: Apr. 26, 1984

[51] Int. Cl.⁴ .............................................. A01H 1/02
[52] U.S. Cl. .................... 47/58; 47/DIG. 1
[58] Field of Search ............................. 47/58, DIG. 1

[56] References Cited

U.S. PATENT DOCUMENTS 2,753,663  7/1956  Jones ....................................... 47/58
3,710,511  1/1973  Patterson ................................. 47/58

OTHER PUBLICATIONS

Duvick, D. N. (1965) Adv. Genet. 13: 1–56.
Singh, A. and J. R. Laughnan (1972) Genetics 71: 607–620.
Levings, S. et al. (1980) Proc. Nat. Acad. Sci. USA 76: 1933–1937.
Shapiro, J. A. (1979) Proc. Nat. Acad. Sci. USA 76: 1933–1937.
Kemble, R. J. and J. R. Bedbrook (1980) Nature 284: 565–566.
Koncz, C. et al. (1981) Mol. Gen. Genet. 183: 449–458.
Kemble, R. J. et al. (1980) Genetics 95: 451–458.
Forde, B. G. et al. (1980) Genetics 95: 443–450.
Beckett, J. B. (1971) crop Sci. 11: 724–727.
Gracen, V. E. and C. O. Grogan (1974) Agron. J. 66: 654–657.
Buchert, J. G. (1961) Proc. Nat. Acad. Sci. USA 47: 1436–1440.
Spruill, W. M., Jr. et al. (1980) Dev. Genet. 1: 363–368.
Pring, D. R. et al. (1977) Proc. Nat. Acad. Sci. USA 74: 2904–2908.
Schuster, A. M. et al. (1983) In: UCLA Symposia on Molecular and Cellular Biology (ed. R. Goldberg) New Series, vol. 12, Plant Molecular Biology, Alan R. Liss, Inc. New York.
Weissinger, A. K. et al. (1982) Proc. Nat. Acad. Sci. USA 79: 1ff.

*Primary Examiner*—R. E. Bagwill
*Attorney, Agent, or Firm*—Lorance L. Greenlee; Robert P. Blackburn

[57] ABSTRACT

Most of the corn in the United States is grown from hybrid seed. The production of hybrid seeds necessitates the emasculation of the desired female parent plant. If this emasculation is carried out by hand, then it becomes a major cost factor. One method to overcome these costs is to obtain inbred lines of corn which have stable cytoplasmic male sterility. Such cytoplasmic male sterility should remain stable when the genome of the inbred line is replaced by the genomes of other inbred lines by backcrossing.

Three major groups of cytoplasmic male sterility (C, T and S) have been extensively studied. In the past the cms S-type has not been extensively utilized in the production of hybrid corn seed because cms S-cytoplasms do not show stable male sterility and also in some backgrounds have a high rate of genetic reversion to male fertility. We describe here the production of a novel stable cytoplasmic male sterile strain (LBN) which remains stably sterile in combination with a large number of inbred corn lines. Some unusual features of this LBN-cytoplasm are described and discussed.

15 Claims, No Drawings

LBN CYTOPLASM

BACKGROUND OF THE INVENTION

Cytoplasmic male sterility (csm) is the most useful maternally inherited trait of higher plants available to breeders. This trait provides a reliable, inexpensive method to emasculate a female parent plant for the production of hybrid seed and is therefore commercially important. Three major types of nuclear/cytoplasmic interactions give rise to cms in corn (*Zea mays L.*). *cms C-, cms T- and cms S-types can be differentiated by nuclear genes that restore pollen fertility to cms-plants*, e.g., a corn inbred strain C0150 has genes which restore fertility only to cms C-types; inbred strain NYD410 restores fertility only to cms T-types and MS64-7 restores fertility only to cms S-types. Fertility restoration in cms S was found to be mediated by a single gene locus Rf3, while T is restored by two gene loci, Rf1 and Rf2 (Duvick, D. N. (1965) Adv. Genet. 13: 1–56; Laughnan, J. R. and S. J. Gabay (1975) in Genetics and Biogenesis of Mitochondria and Chloroplasts, eds. Birky, W. W., Jr. Perlman, P. S. and T. J. Byers (Ohio State Univ. Press, Columbus, OH, pp. 330–349). The standard restorer gene (Rf) for cms-S has been mapped to the long arm of chromosome 2(Gabay-Laughnan, S. J. and J. R. Laughnan (1979) Maize Genet. Coop. Newsletter 53:92–93). Almost all cms corn plants that have been studied can be restored to fertility by one of the above three types.

In the past the three cms types have varied in their commercial significance. Because the cms T-type induced stable sterility (Table 1) in a large number of inbred strains, it was used to produce about 95% of hybrid corn in 1970.

It was, however, quickly abandoned because it was susceptible to race T of the fungus *Helminthosporium maydis*, which destroyed 15% of the U.S. corn crop in 1970. C-type cms sterilizes fewer inbreds than cms T-type but more than cms S-type, and some breeders have replaced cms T-type with cms C-type. The lesson learned from the *H. maydis* epidemic was that wide scale genetic uniformity in crop plants leads readily to selection of specific pathogens. It is therefore important to have a variety of stably sterile cms strains available.

Even though all cms-plants can be categorized into cms C-, cms T- and cms S-types, it is important to recognize that there are genetic differences *within* these types and these variations can be recognized by differences in restoration capacity when the genome of different inbred strains is associated with these male sterile cytoplasms.

LBN cytoplasmic male sterility is a sub-type of the cms S-type. cms S-type cytoplasmic sterility has been known since the 1950's but was not the subject of intensive research until recent years. When the *H. maydis* Race T epidemic of 1970 discredited cms T-cytoplasm, cms S-type did not provide a reasonable alternative because it did not provide stable sterility in association with a wide variety of corn inbreds. Several hundred cases of inherited cytoplasmic changes from cms S-male sterile to a male fertile condition have been identified (Singh, A. and J. R. Laughnan (1972) Genetics 71:607–620). Instead, producers of hybrid corn seed turned to hand detasseling, a mechanical form of emasculation, or to cms C-type, which sterilizes more inbreds than the cms S-type.

cms S-type plants possess two plasmids (S1 and S2) in the mitochondria. S1 has a length of 6.4 kbp and S2 is 5.4 kbp. These plasmids may be involved in the mechanism of cms S-type male sterility, because, in cms-S plants that spontaneously revert to fertility, the plasmids have apparently become integrated in the high molecular weight mitochondrial DNA (hmw mtDNA). S1 and S2 have terminal inverted repeats characteristic of transposable elements. The mitochondrial nucleic acids probably encode the maternally inherited component of cms, because, in corn, differences in cms C-, cms T- and cms S-types are more strongly correlated with differences in mitochondrial DNA (mtDNA) than with differences in chloroplast DNA. These two organelles, mitochondria and chloroplasts, contain maternally-inherited nucleic acids of plants. Leaver et al. (Leaver, C. J. and M. W. Gray (1982) Ann. Rev. Plant Physiol.) found that in the cms-T system, a mitochondrially-encoded protein unique to cms-T is changed when nuclei containing cms-T restorer genes are introduced. These observations support the hypothesis that restoration of fertility in cms plants results from interaction between mitochondrial and nuclear gene products.

There is a strong correlation between the S1 and S2 DNA's and cms-S (Levings, S. et al (1980) Science 209:1021–1023). The mtDNA of seven cms-S revertants to fertility were analysed. It was found that the S1 and S2 plasmids had virtually disappeared in all seven revertant strains and this disappearance was associated with the presence of new fragments in restriction endonuclease digests of the hmw mtDNA. Labelled probes of S2 DNA hybridized to some of these new bands. Further evidence suggesting that the S1is important in reversions to fertility was the quantitative decrease of S2 in M825 (the sweet corn inbred that produced the highest reversion rate). S1 and S2 plasmids usually occur in equimolar quantities in cms-S mitochondria but in the M825 nuclear association, the S2 is decreased in amount. The implication was that the fertility of the revertants was caused by integration of S2 or by the mtDNA rearrangements resulting from the integration and that cms-S was related to the non-integrated state of the plasmids. More recent studies have shown that sequences homologous to those of S1 and S2 plasmids are integrated in the hmw mtDNA of other non-sterile ("normal") cytoplasms thus supporting the idea that integration of S1 and S2 is correlated with fertility.

However, the role of S1 and S2 is not clear. S1 and S2 hybridize to the hmw mtDNA of S-sterile as well as that of normal and revertant cytoplasms. If plasmid integration into hmw mtDNA does result in fertility, then an analogy to transposable element systems might explain the presence of S1 and S2 sequences in hmw mtDNA of S-sterile plants (Levings, C. S. III, et al. (1980) Science 209:1021–1023). Certain transposable elements duplicate themselves in the process of excising, leaving the duplicate copy in the original site (Shapiro, J. A. (1979) Proc. Nat. Acad. Sci. USA 76:1933–1937). Levings, et al. (supra) concluded that "the presence in the mitochondrial DNA of sequences homologous to the S1 and S2 DNA's after their excisions would be anticipated if excision events behave similarly [to the prokaryotic system]". But the question of whether the integrated or non-integrated state of the plasmids has anything to do with male sterility has not been settled.

Another report (Weissinger, A. K., et al. (1982) Proc. Nat. Acad. Sci. USA 79:1–53) identified two other plasmids, R1 and R2, in non-sterile cytoplasms from 12 races of South American maize. R2 appears to be identical to S2 in size and restriction sites. R1 contains most of S1 plus 1000 additional base pairs. R1 and R2, like S1 and S2, have terminal inverted repeats of approximately 150 base pairs. The hmw mtDNA of the R-containing cytoplasms was markedly different from the hmw mtDNA of cms-S, as shown by the patterns of restriction digests.

Other low molecular-weight mtDNA's (lmw mtDNA) in addition to S1 and S2 occur in "normal" and the three cms cytoplasms: C-, T- and S- cytoplasm (Kemble, R. J. and J. R. Bedbrook (1980) Nature 284:565–566). One of these lmw mtDNA's, which is found in all cytoplasms, exists in linear (L), open circular (OC) and supercoiled (CCC) forms. Another, named "T" (36, 51) is 2.3 kbp long in N-, cms C- and cms S- cytoplasms and 2.0 kbp long in cms T-cytoplasm. Koncz, -et al. [(1981) Mol. Gen. Genet. 183:449–458] reported that S2 probes hybridize strongly to these 2.0 - 2.3 kbp DNA's. Finally, C-cytoplasm alone has two additional circular DNA's (called "C") approximately 1600 and 1400 bp long. The role, if any, of these various lmw mt DNA's in the cms phenomenon is unknown.

To summarize, the best evidence for the involvement of the S-plasmids in cms comes from the analysis of seven revertants to non-sterile cytoplasm. In these seven cytoplasms, the S1 and S2 DNA's disappeared, new bands appeared in restriction digests of the hmw mtDNA and S2 probes hybridized to some of these new bands. Nevertheless, the precise relation (if any) of S1 and S2 to cms-S or to the reversion to fertility is unclear.

The main evidence supporting the correlation between the S-bands and cms-S (Kemble, R. J. et al. (1980) Genetics 95:451–458; Forde, et al. (1980) Genetics 95:443–450) involved the analysis of a large number of cms cytoplasms which mostly originated from the Cornell collection. All cms strains that had been identified as cms-S by the restoration gene pattern contained the S1 and S2 bands and also had a characteristic set of mtDNA in vitro translation products. B and D, which are male-sterile cytoplasms previously left unclassified (Beckett, J. B. (1971) Crop. Sci. 11:724–727; Gracen, V. E. and C. O. Grogan (1974) Agron. J. 65:654–657) because of unusual restoration patterns, were also found to have the S-bands and the in vitro translation products characteristic of S. All other cytoplasms could be classified as cms T-, cms C-, "normal" or EP (from teosinte).

Another characteristic that distinguishes cms S from cms T and cms C is gametophytic restoration (Buchert, J. G. (1961) Proc. Nat. Acad. Sci. USA 47:1436–1440). In a gametophytic system, plants are restored to fertility at the level of the gametophyte, i.e., the pollen grain. When a cms-S plant heterozygous for nuclear restorer genes produces pollen, then only pollen containing the restorer (Rf) allele develops normally. Pollen in the same tassel containing the non-restoring (rf) allele aborts. In contrast, fertility restoration of cms-C and cms-T is sporophytic. All pollen of Rf rf plants develops normally in a sporophytic system, even though half of the pollen does not carry the Rf allele. Thus the pollen viability is determined by the nuclear genotype of the mother plant, i.e., the sporophyte.

There are thus four criteria to distinguish cms-S: (1) presence of S1 and S2; (2) in vitro translation products of mtDNA; (3) gametophytic restoration; and (4) restriction digest patterns of mtDNA.

SUMMARY OF THE INVENTION

Cytoplasmic male sterility in corn and other crop plants has been of great use to breeders because the trait obviates the necessity of hand emasculation of one parent. In past research on corn lines, the cytoplasmic male sterile type-T was used but use was discontinued when it was found that type-T was susceptible to fungal infections. Some use has been made of cms-C cytoplasmic male sterility but cms-S cytoplasmic male sterility was largely ignored because instability of its sterility in association with a wide variety of inbred genomes and because of a high rate of genetic reversion.

The present invention describes the breeding of a derivative cytoplasm (LBN) of an cms S-type cytoplasm in which the property of male sterility is remarkably stable in a wide variety of economically important inbred corn lines and in which the rate of genetic reversion is very low. Some unusual and unexpected properties of the LBN-cytoplasm are described and discussed in relation to the art of corn breeding.

DETAILED DESCRIPTION OF THE INVENTION

Until 1970, when an epidemic of *Helminthosporium maydis* Race T caused widespread loss in the U.S. corn crop, cms-T was used almost exclusively by corn breeders to produce hybrid seed. Following the epidemic cms-T was abandoned but cms-C and cms-S were not extensively used because they did not promote stable sterility in a wide variety of inbred corn strains. In addition to this variation in the genetics of restoration, the cms S-cytoplasms have also shown unusual instability. Several hundred cases of inherited cytoplasmic changes from cms S-male sterile to a male fertile condition have been identified (Singh, A. and J. R. Laughnan (1972) Genetics 71:607–620).

Nevertheless, because of the economic advantages breeders have continued the search for cms lines. The cms-S category has produced the least number of stable male sterile lines so the identification and analysis of the very stable LBN-cms among a number of cms-S inbred nucleus/cms-S cytoplasm combinations was unexpected. LBN-cms has a number of unique features which are described below.

The Plant Breeding Department at Cornell University maintains a collection of 36 sources of maize cytoplasms which can confer the trait of male sterility (Sisco, P.H. et al (1982) Maize Genet. Coop. Newsletter 56:80; Gracen, V. E. and C. O. Grogan (1974) Agron. J. 65:654).

Twenty-five of these cytoplasms belong to the cms S-group. Twenty-four cms-S cytoplasms were examined by screening for the presence of the S1 and S2 plasmids. In one strain with the inbred nucleus/cytoplasm combination W182BN(L), screening for the S-plasmids revealed the presence of two additional nucleic acid plasmids. This combination of L-cytoplasm with inbred strain W182BN was obtained by crossing strain 38-11(L) (Beckett, J. B. (1971) Crop Sci. 11:724-727) to strain W182BN and then backcrossing the F1 to W182BN for fifteen generations. These additional nucleic acid plasmids are now called the "LBN-bands" or "LBN-plasmids". The 38-11 nucleus had also been replaced in a similar manner with inbred genomes from a number of other inbred corn lines. The LBN-plasmids were not found in any of these other L-cytoplasm/inbred line nucleus combinations suggesting that their presence is a novel and unexpected feature of the W182BN(L) combination and also that the two new nucleic acid plasmids were not present in the original 38-11(L) cytoplasmic male sterile strain. Strain 38-11(L) is no longer available. The unique combination of W182BN nuclei and L-cytoplasm has been renamed W182BN(LBN), i.e., L-cytoplasm as it exists in W182BN. The male sterility of this W182BN(LBN) is remarkably stable and full fertility can be regained by crossing it to any corn line containing the Rf$_3$ restorer gene. Such a strain is ideal for the production of hybrid corn. A corn line containing the rf3 non-restorer gene will not confer fertility on the W182BN(LBN) line when the rf3 containing line is used as the male parent and the W182BN(LBN) is the female parent.

The various nucleic acid plasmids were identified as described (Example 1). Plasmids recovered in order from the slowest migrating to the fastest were:
1. High molecular-weight DNA, which included the mitochondrial "chromosomes" (Spruill, W. M., Jr., et al. (1980) Dev. Genet. 1:363–378).
2. The S1 and S2 plasmids (Pring, D. R., et al. (1977) Proc. Nat. Acad. Sci. U.S.A. 74:2904–2908).
3. OC, the open-circular form of a low-molecular-weight DNA species found in all cytoplasms (Kemble, R. J. and J. R. Bedbrook (1980) Nature 284:565–566; Koncz, C. et al. (1981) Mol. Gen. Genet. 183:449–458).
4. Single-stranded RNA's, primarily ribosomal and messenger RNA's.

The plasmids described above recurred in all 24 cms-S strains tested. Unexpectedly one of the strains, i.e., the inbred/cytoplasm combination W182BN(L), (see above) possessed two extra bands which have been labelled LBN1 and LBN2. A series of experiments was undertaken to determine their size, nucleic acid composition and location in the cell. The nuclear background of the cytoplasm containing the LBN bands was found to affect their intensity in a gel. Because L cytoplasms other than W182BN(L) did not have the LBN plasmids, the L-cytoplasm containing the bands was renamed LBN cytoplasm, for "L cytoplasm as it exists in inbred W182BN".

A number of experiments were done to determine the nucleic acid composition of the LBN plasmids (Example 2). All of these experiments indicated that the LBN1 and LBN2 plasmids were dsRNA: (1) RNase-free DNase I did not affect the LBN-bands on the agarose gels; (2) RNase III, which is active on dsRNA, eliminated all except a faint remnant of LBN1; (3) RNase "Mix" in high salt conditions (active on ssRNA) completely digested ribosomal and messenger RNA controls but had no effect on the LBN bands.

The molecular weight of the unique LBN nucleic acids was estimated from their mobilities in agarose gel electrophoresis with various known dsRNA's and dsDNA's as standards. The weights were estimated to be: (1) LBN1 ; $1.8 \times 10^6$ using the dsDNA markers and $1.9 \times 10^6$ using the dsRNA markers; (2) LBN2; $0.52 \times 10^6$ using the DNA markers and $0.27 \times 10^6$ using the dsRNA markers.

Since these two novel nucleic acid plasmids are dsRNA, the question may be asked "Are they of viral origin". The estimated total molecular weight is $2.4 \times 10^6$ daltons. Since only one strand usually codes for polypeptide synthesis, there is approximately $1.2 \times 10^6$ daltons worth of coding capacity, i.e., less than the coding capacity of the smallest known plant virus, Southern bean mosaic virus, which has a coding capacity of $1.4 \times 10^6$ daltons (Siegel, A. et al. (1974) In "Reproduction of small plant RNA viruses", H. Fraenkel-Conrat and R. R. Wagner (eds.) Comprehensive virology Vol. II Plenum Press, New York).

Smaller infectious agents called viroids also occur in plants. They are composed of RNA but do not resemble the LBN1 and LBN2 bands. In addition the average size of viroids is only $0.1 \times 10^6$ daltons which is 20 times smaller than LBN1 and 5 times smaller than LBN2. Viroids are cleaved by RNase A in high salt conditions but are not affected by RNase III (Diener, T. O. (1980) Stadler Symp. 12:123–141). This digestion pattern is the opposite of that found for the LBN-plasmids.

Gemini viruses, which are slightly larger in molecular weight than LBN2, are ssDNA's (Haber, S. et al. (1981) Nature 289:324–326). Thus their total coding capacity is approximately $3.6 \times 10^6$ daltons, which is much larger than LBN1 and LBN2 combined.

No firm evidence has been found that LBN1 and LBN2 are viral in origin.

Electron microscopy of leaf tissue extracts of LBN-cytoplasm failed to reveal any virus-like particles. LBN-plasmids also have no resemblance to the dsRNA in the spherical bodies associated with cytoplasmic male sterility in *Vicia faba* (Edwardson, J. R. et al. (1976) Genetics 82:443–449; Grill, L. K. and S. J. Garger (1981) Proc. Nat. Acad. Sci. USA 78:7043–7046). These bodies, about 70 nm in diameter, are visible in the electron microscope and contain an RNA species whose molecular weight has been estimated between 10 and $13 \times 10^6$ daltons (i.e., 5–6 times larger than LBN1). The sterility associated with these bodies is quite unlike that found in corn. In cytoplasmic male sterile *Vicia faba* plants restored to male fertility, the virus-like spherical bodies disappear. The restored plants and their progeny remain male-fertile, unless the plants are re-inoculated by some mechanical means. Since the spherical bodies and the associated sterility can be transmitted by dodder, the system in *Vicia faba* is most easily explained as a virus-induced form of sterility.

The function of the LBN1 and LBN2 bands remains a mystery. Double stranded RNA is known to inhibit protein synthesis (Burke, D. C. (1977) Trends Biochem. Sci. 2:249–251). The LBN dsRNA's are associated with mitochondria in very stably male sterile cytoplasms and mitochondrial defects are the cause of male sterility in corn; therefore it is likely that LBN dsRNA's have an effect on male sterility.

Schuster, et al. (Schuster, A. M., et al. (1983) In UCLA Symposia on Molecular and Cellular Biology, (ed. R. Goldberg) New Series, Vol. 12. Plant Molecular Biology, Alan R. Liss, Inc., New York) have recently reported that ssRNA's homologous to the LBN dsRNA's are present in other S-type cytoplasms and in RU, a cytoplasm not associated with male sterility (Weissinger, A. K., et al. (1982) Proc. Nat. Acad. Sci. USA 79:1–5). The LBN dsRNA's may represent a replicative form (RF) of these ssRNA's, as are found in many plant viruses (Siegel, A., et al. (1974) In Comprehensive Virology (eds. H. Fraenkel-Conrat and R. R. Wagner) Vol. 2, Plenum Press, New York).

The LBN bands were first found in the 12,000 g fraction of etiolated W182BN(LBN) coleoptiles prepared according to the standard rapid assay for S-plasmids (Kemble, R. J. and J. R. Bedbrook (1979) Maydica 24:175–180). This fraction is enriched for mitochondria but also contains fragments of nuclei, etioplasts and other cellular components. In order to show with greater confidence that LBN-plasmids were associated with mitochondria, it was necessary to further purify the mitochondria. The pelleted 12,000 g fraction was resuspended in buffer and centrifuged again for 10 minutes at 12,000g in a tube having a 0.6 M sucrose pad. The pellet at the bottom of the tube was then prepared according to the rapid assay (supra) and electrophoresed on a gel. The LBN bands were very prominent on these gels. Since centrifuging through a 0.6M sucrose pad is one of the best methods for obtaining mitochondria free of contaminants, it was concluded that the LBN-plasmids are associated with the mitochondria. Electron microscopy of this purified 12,000 g pellet and of cell sap components failed to reveal any virus-like particles attached to or comigrating with the mitochondria.

The concentrations of LBN1 and LBN2 vary in the presence of different nuclei from various inbred strains. These two dsRNA's were first found in W182BN(LBN), which had been used as a source of cytoplasm for ten inbreds (Table 1). Several backcross generations of the inbreds were analysed with the assay for S-plasmids (Kemble, R. J. and R. J. Bedbrook (1980) Nature 284:565–566) to study the effect on the LBN bands when the W182BN genotype was replaced by that of the other inbreds. The concentration of LBN nucleic acids was judged by comparing the brightness of the LBN bands with the brightness of the S1 and S2 bands in the same lane. The brightness of the S1 and S2 bands was quite constant in different genomic environments. In W182BN(LBN) the LBN bands were brighter than the S1 and S2 bands. The results of a number of experiments showed obvious differences in intensity of the LBN bands among inbred and backcross generations (Table 2). The ten inbreds are listed in order of the LBN band intensity. In one case, using inbred 2132, the intensity of the dsRNA bands was as great as with inbred W182BN, thus indicating that a high concentration of dsRNA (LBN1 and LBN2) was an unusual but not unique feature of the cytoplasmic interaction with various inbred nuclei. In the remaining examples, dsRNA band intensity decreased. Where band intensity decreased rapidly between generations (e.g. NY327 BC$_2$ and NY327 BC$_3$), several ears from each generation were analysed to look for variation in band intensity within generations. No differences within generations were found.

After three generations of backcrossing, the LBN nucleic acids in eight of the ten inbreds had decreased to the point where they were not visible under the usual conditions of the rapid assay (i.e., where nucleic acids were not concentrated by ethanol precipitation). However, in all backcrosses examined, when the nucleic acids were additionally purified by an additional step of phenol extraction and ethanol precipitation, the dsRNA's (LBN1 and LBN2) were shown to still be present in small amounts. In order to decide whether the LBN had irreversibly decreased or whether the concentration could be increased again by crossing W182BN and 2132 nuclear genomes back into the cytoplasm, the last available backcross generation of each inbred was crossed as female to W182BN and 2132. LBN nucleic acids increased in all eight cases (supra) as the W182BN or 2132 genomes increasingly replaced the various other inbred genomes. The concentration of the LBN dsRNA's increased with each successive cross to W182BN or to 2132, particularly in the backcrosses to 2132. Thus the presence of the dsRNA's and the very stable male sterility appears to be the result of a unique interaction between particular nuclei and the LBN cytoplasm.

When the rapid assay for the S-plasmids revealed unique nucleic acid species in W182BN(LBN), a search was made for traits that might be associated with that inbred/cytoplasm combination. In a first test, W182BN(LBN) was the only S-type cytoplasm that produced a sterile F1 in crosses with the partial restorer C0192. (Note: C0192 does not carry an Rf3 restorer gene.) All other W182BN S-types tested—B, CA, D, EK, G, H, I, J, K, M, ML, PS, S, TC and VG(=K)—had produced F1's that were rated "5", fully fertile. A second test was run in which, in addition to the cytoplasms tested in the first test, other cytoplasms were tested, including IA, R and TA. Ratings were similar to those of the first test, with W182BN(LBN)×C0192 being fully sterile. LBN cytoplasm also promotes complete cms in a number of economically important inbred strains, e.g., Mo17, FR22 and FR23.

There are two methods to measure "male sterility" in corn. One method of distinguishing male sterility is by pollen abortion, i.e., pollen sterility, while the other method is to measure the extent of anther exsertion, i.e., functional sterility. A complete lack of anther exsertion would result in complete functional sterility. Although LBN cytoplasm was clearly functionally sterile in this hybrid (i.e., W182BN(LBN)×C0192), dissection of its florets showed that it had a small percentage of normal appearing pollen. The percentage was the same as found in the standard S-types that had the thin anthers exserted, i.e., ca. 5%. In hybrid production fields, lack of anther exsertion is the desired phenotype of the female inbreds and thus LBN would be the cytoplasm of choice. The relationship of its lack of anther exsertion to its smaller percentage of normal pollen is not clear. Perhaps the unique dsRNA's of LBN cytoplasm have an effect on anther exsertion as well as on pollen fertility.

Both D. F. Jones, et al. (Jones D. F., et al. (1943) Proc. Amer. Soc. Hort. Sci. 43:189–194) and Duvick (Duvick, D. N. (1965) Adv. Genet. 13:1–56) have noted the fact that anther exsertion and pollen fertility are not always well correlated. Jones, et al., found tassels in which all the pollen appeared normal, yet no anthers were exserted. Duvick reported that the opposite often occurs in S-steriles, i.e., many anthers are exserted but no functional pollen is present.

W182BN(LBN) did not differ from W182BN in other cytoplasms with respect to plant height, ear height or other fross morphological features. The one trait which did correlate with LBN cytoplasm was male sterility. The extra degree of male sterility of LBN cytoplasm was apparent in a series of single crosses to the inbred C0192, which partially restores fertility to S-steriles:

W182BN (most S-types)×C0192=plants which exsert thin anthers.
W182BN(LBN)×C0192=plants fully male sterile (no exserted anthers).

However, inbreds which fully restore fertility to S-cytoplasm also restored W182BN(LBN). These inbreds can be assumed to carry an Rf3 restorer gene.

By extensive backcrossing to a variety of available inbred maize lines, a number of inbred nucleus/LBN cytoplasmic combinations have been obtained. As shown (Table 3) a large number of these combinations exhibited complete and stable male cytoplasmic sterility, thus demonstrating the utility of the LBN cytoplasm in the production of many different hybrid maize strains.

EXAMPLE 1

Detection of plasmids by agarose gel electrophoresis

The methods used were essentially those described in Kemble and Bedbrook (Kemble, R. J. and R. J. Bedbrook (1979) Maydica 24:175-180) except that, following a suggestion by John Carlson, University of Illinois, the grinding buffer was changed to : 0.8 M Tris-Base (pH 8.3), 0.4 M sodium acetate and 0.04 M EDTA. This buffer gave a better yield of plasmid DNA.

Electrophoresis was done using a gel apparatus where the horizontal slab gel was submerged under buffer. Long gels (30+cm) were used with as low a current as time allowed (<1 volt/cm). The wavelength of UV light in the trans-illiminator used to photograph the gels also affected the results. Short wavelengths (260 nm) made the individual bands brighter but also caused breaks in the nucleic acids since such short wavelengths "excited" the ethidium bromide used as a strain. Such breakage was a problem if the gels were to be run longer or if the nucleic acids were to be eluted from the gel after exposure to the short wave UV. Longer UV wavelengths (360 nm) do not cause breakage but have poorer resolving power. A compromise was to use a trans-illuminator with a wave-length of 300 nm.

EXAMPLE 2

Determination of nucleic acids composition of plasmids

The nucleic acid composition of the LBN bands was determined by digesting them with a series of nucleases. The inbred W182BN(LBN) and a single cross W182BN(LBN)×inbred strain 2132 were used as a source of LBN nucleic acids. In the first experiment, LBN nucleic acids were digested with RNase in low salt conditions (i.e., no standard saline citrate (SSC) added) so that all RNA would be eliminated. It was evident from the gels that the LBN bands had virtually disappeared, although the LBN2 band was slightly resistant.

In further experiments DNase-free RNase "Mix" (i.e., 500 μg/ml RNase A and 25 μg/ml RNase T were used in high salt (2×SSC) and low salt (no SSC) conditions. Under low salt conditions, all RNA is cleaved by the RNase enzymes, but in high salt conditions, dsRNA resists digestion (Diener, T. O. (1980) Stadler Symp. 12:123-141). In these experiments the LBN unique RNA's remained in high salt conditions, indicating that they were double stranded. RNase III is specific for dsRNA and requires approximately 18-25 base pairs consecutively bonded to cleave RNA (see supra). Nucleic acid samples were digested in the following mixture: 30 mM Tris-HCl pH 8.0, 100 mM NaCl, 5mM $MgCl_2$, 1 mM EDTA, 1 mM dithiothreitol (Ferrari, S. et al. (1980) Proc. Nat. Acad. Sci. USA 77:2395-2399) containing 18 μl RNase III (concentration per μl was unspecified). The mixture was incubated at 37° C. for 30 minutes and loaded onto the gel immediately. It was concluded that LBN1 and LBN2 were dsRNA plasmids because RNase III treatment totally eliminated the LBN2 band and left only a faint trace of LBN1.

In yet another experiment, the nucleic acids of the LBN bands were digested in 25 mM Tris-HCl pH 7.0 containing 100 mM $MgCl_2$ and 10 μg/ml Rnase-free DNase I (1mg/ml). The reaction mix was incubated at 37° C. for 30 minutes and loaded onto a gel immediately. This treatment digested the S-plasmids and the OC-plasmids but did not affect the LBN-plasmids or the ssRNA and ds RNA controls.

EXAMPLE 3

Production of hybrid corn by use of the inbred nucleus/cytoplasm combination W182BN(LBN)

If W182BN(LBN) is the inbred strain which is to be used as the female parent in the production of hybrid corn, then it can be crossed to any other inbred line which carries an Rf3 restorer gene to give a single cross hybrid. These two parent inbred strains are each essentially genetically homozygous. If a double cross hybrid is desired, then the male parent in the first cross must not carry an Rf3 restorer gene but the male parent in the second cross must carry such a gene. The progeny of such a first cross will be genetically heterozygous.

If other inbred nuclei are desired to be used with the LBN cytoplasm as the female parent, then the W182BN nucleus must be replaced by the desired inbred nucleus. This can be done by crossing W182BN(LBN) to the desired inbred, e.g., Mo17, and then backcrossing the F1 to the desired inbred for a number of generations. When the W182BN nucleus has been replaced by the nucleus of the desired inbred, the plasmid profile is examined as described (Example 1) and the sterility of the new inbred (LBN) cytoplasm is checked. In the event that the cytoplasm of the new inbred (LBN) does not demonstrate the presence of LBN1 or LBN2, then the new inbred (LBN) combination is crossed to either W182BN or 2132 and the plasmid profile of this cross is examined. In all instances examined to date, the presence of LBN1 and LBN2 has been demonstrated. Therefore, the presence of LBN1 and LBN2 in the plasmid profiles of any nucleus/cytoplasm combination tested in this fashion is diagnostic of LBN cytoplasm in the male sterile parent. Such a cross is designated herein as a dsRNA test cross.

TABLE 1

Fertility ratings of 38 male-sterile cytoplasms in 28 Inbred backgrounds[a]

| Inbreds Cytoplasms | A239 | A495 | A619 | A632 | A636 | AyX145 | AyX157 | AuX187y-2 | Ay499 | Ay303E | Ay490-2A | B8 | C153 | CO150 | CO192 |
|---|---|---|---|---|---|---|---|---|---|---|---|---|---|---|---|
| C Group | | | | | | | | | | | | | | | |
| C | 1[b] | 5 | 5 | — | — | 5 | 1 | 5 | 5 | 3 | 1-5 | 1 | 5 | 5 | 5 |
| RB | 1-3 | 5 | 5 | 1-3 | 5 | 5 | 1 | 5 | 5 | 3 | 1 | — | 5 | 5 | 5 |
| T Group | | | | | | | | | | | | | | | |
| HA | 1 | 1 | 1 | 1 | 1 | — | 1 | 5 | 1 | 1-3 | 1 | 1 | 5 | — | 2 |

TABLE 1-continued

Fertility ratings of 38 male-sterile cytoplasms in 28 Inbred backgrounds[a]

| | | | | | | | | | | | | | | | |
|---|---|---|---|---|---|---|---|---|---|---|---|---|---|---|---|
| P | 1 | — | 3 | — | — | — | — | 5 | — | — | — | 1 | 5 | — | 3 |
| Q | 1-3 | — | 1 | 1 | 1 | 1 | 1 | 5 | 1 | 2 | 1 | 1 | 5 | — | 1 |
| RS | — | 1 | 1-3 | — | 1 | 1 | — | 5 | 1-2 | 1 | 1 | 3 | 5 | 1 | 2 |
| T | 1 | 1 | 1 | 1 | 1 | 1 | 1 | 5 | 1 | 1 | 1 | 1 | 5 | 1 | 2 |

S Group

| | | | | | | | | | | | | | | | |
|---|---|---|---|---|---|---|---|---|---|---|---|---|---|---|---|
| CA | 5 | — | 5 | 3 | 3 | 2 | 3 | 3 | 1 | 3 | 1 | 1 | 2 | — | 3 |
| EK | 1 | 5 | 3 | 3 | 3 | 3 | 5 | — | 2 | 3 | 1-3 | 2 | 4 | 1 | 3 |
| G | 1 | 5 | 5 | 1-3 | 2-4 | — | 3 | 3 | 1 | 3 | 1 | 3 | 3 | 1 | 3 |
| H | — | 1-3 | 5 | — | — | 2 | 3 | 3 | 2 | 3 | 1 | 3 | — | 2 | 3 |
| I | — | 3 | 3 | 1-3 | — | 1-3 | 3 | 3 | 3 | 3 | 3 | 3 | 3 | 2 | 3 |
| IA | — | 3 | 3 | 3 | 3 | — | 3 | 3 | 2 | — | 1 | 3 | 3 | 1 | 3 |
| J | 1 | 3 | 3 | 1-3 | 3 | 1-3 | — | 5 | 1 | 3 | 1 | 3 | 5 | — | 3 |
| K | 1 | — | 5 | 3 | 5 | — | 3 | 2 | 2 | 3 | 1 | — | 3 | 1 | 3 |
| L | 5 | — | 3 | 5 | 5 | 2 | 5 | 5 | 5 | 5 | 5 | 3 | — | 1 | 1 |
| M | 5 | — | 3 | 1-3 | 3 | — | — | 5 | — | — | 2 | 3 | 3 | — | 3 |
| ME | 5 | — | 3 | 1-3 | 3 | 2 | 3 | 1 | 2 | — | 5 | 3 | 2 | — | 3 |
| ML | 1 | 5 | 3 | 3 | 3 | 1-3 | 3 | 3 | 2 | 3 | 1-3 | 3 | 3 | 1 | — |
| MY | 2 | 2 | 3 | 1-3 | 3 | 5 | 1-3 | 5 | 1 | — | 1 | 3 | 3 | 1 | 3 |
| PS | 3 | 3 | 3 | 1-3 | 3 | 5 | 3 | 1 | 2 | — | 1 | 2 | 3 | 1 | 5 |
| R | — | 3 | 5 | — | — | 1-3 | — | 3 | — | — | — | 3 | 5 | — | 3 |
| F | — | 1-3 | 5 | — | 1-3 | — | — | 3 | — | — | — | 5 | 3 | — | 3 |
| S | 1 | — | 5 | 3 | — | — | — | 3 | — | — | — | 3 | 3 | — | 3 |
| SD | 1 | — | 5 | 1 | 3 | — | 3 | 3 | 1 | 2 | 1 | 1 | 3 | — | 3 |
| TA | 1 | 3 | 5 | 3 | 3 | 3 | — | 3 | — | — | — | 3 | 3 | 1 | 1 |
| VG | — | 3 | 5 | — | — | — | — | 3 | — | 3 | — | 3 | 3 | 1 | 3 |
| W | — | 1-3 | 5 | — | — | 2 | — | 3 | — | — | — | 3 | 4 | 1 | 3 |

Unclassified

| | | | | | | | | | | | | | | | |
|---|---|---|---|---|---|---|---|---|---|---|---|---|---|---|---|
| B | — | 1 | 5 | — | — | — | — | 5 | — | 3 | — | 5 | 5 | 1 | 5 |
| OH | — | — | 5 | 5 | 5 | — | 3 | 5 | 3 | — | 5 | 5 | — | — | 3 |
| D | 1-3 | 1 | 5 | 5 | — | 3 | 3 | 5 | — | — | 5 | 5 | 5 | — | 5 |
| EP | 5 | — | 1 | 5 | 5 | — | 3 | 5 | — | — | 5 | 5 | — | — | 5 |
| LF | 1 | — | 3 | 3 | 3 | 5 | — | 5 | 5 | — | 5 | 5 | 5 | — | 5 |

N Group

| | | | | | | | | | | | | | | | |
|---|---|---|---|---|---|---|---|---|---|---|---|---|---|---|---|
| NT | — | — | 5 | 5 | 5 | — | 5 | 5 | 5 | — | 5 | 5 | — | — | 5 |
| OY | 5 | — | — | 5 | 5 | — | 5 | 5 | 5 | — | 5 | 5 | 5 | — | 5 |
| SG | 5 | 5 | 5 | 5 | 5 | — | 5 | 5 | 5 | — | 5 | 5 | 5 | — | 5 |
| 181 | 5 | 5 | 5 | 5 | 5 | — | 5 | 5 | 5 | — | 5 | 5 | 5 | — | 5 |
| 234 | 5 | 5 | 5 | 5 | 5 | — | 5 | 5 | 5 | — | 5 | 5 | 5 | — | 5 |

| Inbreds-Cytoplasms | CrS4HLA | MS89A | MS1334 | NYD410 | NY63-71-1 | NY821 | NY821LERf | Oh43 | Oh51A | SD10 | Va20 | W64A | W182BN |
|---|---|---|---|---|---|---|---|---|---|---|---|---|---|

C Group

| | | | | | | | | | | | | | |
|---|---|---|---|---|---|---|---|---|---|---|---|---|---|
| C | 5 | — | 5 | 1 | — | 5 | 3-5 | 5 | 1 | — | 5 | 5 | 1 |
| RB | 3 | 2-4 | 5 | 1 | 1 | 5 | 5 | 5 | 1 | 1 | 5 | 5 | 1 |

T Group

| | | | | | | | | | | | | | |
|---|---|---|---|---|---|---|---|---|---|---|---|---|---|
| HA | 1 | 1 | 1 | 3 | 1 | 1 | 5 | 1 | 1 | 1 | 1 | 1 | 1 |
| P | 1 | 3 | — | — | — | 5 | 3 | — | 3 | — | 1 | — | 1 |
| Q | 1 | 1 | 1 | 5 | — | 1 | 5 | 1 | 1 | — | 1 | 1 | 1 |
| RS | 1 | 1 | 1 | 5 | — | 1 | 5 | 1 | 1 | 1 | 1 | 1 | 1 |
| T | 1 | 1 | 1 | 5 | 1 | 1 | 5 | 1 | 1 | 1 | 1 | 1 | 1 |

S Group

| | | | | | | | | | | | | | |
|---|---|---|---|---|---|---|---|---|---|---|---|---|---|
| CA | 1 | 3 | 3 | 1 | — | 3 | 5 | 5 | 5 | 1 | 5 | 2 | 1 |
| EK | 3 | 2 | 3 | — | 1 | 3 | 5 | 5 | 3 | 2 | 5 | 2 | 1 |
| G | 1 | 3 | 2 | 1 | 2 | 2 | 5 | 5 | 5 | — | 5 | 2 | 1 |
| H | 1 | 1 | 3 | 1 | 2 | 2 | 5 | — | 3 | — | 5 | 1 | 1 |
| I | 1 | 3 | 3 | 1 | 2 | 3 | 5 | 3 | 3 | 2 | 5 | 5 | 1 |
| IA | 1 | — | 3 | 2 | 1 | 3 | 5 | 5 | 3 | 2 | 3 | 2 | 1 |
| J | 3 | 2 | 3 | — | — | 3 | 5 | — | 3 | — | 5 | 3 | 1 |
| K | 3 | — | 3 | 1 | 2 | 3 | 5 | 5 | 3 | 2 | 5 | 1 | 1 |
| L | 5 | 5 | 3 | 5 | — | 5 | 5 | 3 | 5 | 5 | 5 | — | 1 |
| M | 3 | 3 | — | — | — | 3 | 5 | 3 | 3 | — | 5 | 1 | 1 |
| ME | 5 | 2 | 3 | 1 | — | 2 | 5 | 5 | 5 | 2 | 3 | 2 | 5 |
| ML | — | 3 | 3 | 1 | 2 | 1 | 5 | 3 | 3 | 2 | 5 | — | 1 |
| MY | 3 | 3 | 2 | 1 | 2 | 2 | 5 | 3 | 5 | 2 | 5 | 1 | 5 |
| PS | 1 | 2 | 3 | 1 | 2 | 2 | 5 | 5 | 3 | 3 | 5 | 2 | 1 |
| R | 3 | — | — | — | — | 2 | 5 | — | 3 | — | 3 | — | 1 |
| F | 5 | — | — | — | — | 5 | 5 | — | 3 | — | 3 | — | 5 |
| S | 1 | 2 | — | — | — | 3 | 5 | — | 3 | — | 5 | 3 | 1 |
| SD | — | 2 | — | 1 | — | 1 | 5 | 3 | 3 | 2 | 5 | 2 | 1-3 |

TABLE 1-continued

Fertility ratings of 38 male-sterile cytoplasms in 28 Inbred backgrounds[a]

| | | | | | | | | | | | | |
|---|---|---|---|---|---|---|---|---|---|---|---|---|
| TA | 5 | 2 | — | — | — | 3 | 5 | — | 5 | — | 5 | 2 | 1 |
| VG | 1 | — | — | — | — | 3 | 5 | — | 3 | — | 5 | — | 1 |
| W | 5 | — | — | — | — | 3 | 5 | — | 3 | — | 5 | — | 1 |
| Un-classified | | | | | | | | | | | | |
| B | 5 | — | — | — | — | 5 | 5 | — | 5 | — | 5 | — | 1–3 |
| OH | 5 | 5 | — | 5 | — | 3 | 5 | 5 | 5 | 5 | — | 5 | 5 |
| D | 3 | 1–3 | 3 | 1 | 2 | 3 | 5 | 5 | 5 | 3 | — | 3 | 2 |
| EP | 5 | 3 | — | 5 | — | 5 | 5 | — | 3 | 5 | 3–5 | 5 | 5 |
| LF | 5 | 3 | 5 | 5 | 5 | 5 | 5 | 5 | 5 | 5 | — | 5 | 3 |
| N Group | | | | | | | | | | | | |
| NT | 5 | 5 | 5 | 5 | — | 5 | 5 | 5 | 5 | 5 | 5 | 5 | 5 |
| OY | 5 | 5 | 5 | 5 | 5 | 5 | 5 | 5 | 5 | 5 | 5 | 5 | 5 |
| SG | 5 | 5 | 5 | 5 | 5 | 5 | 5 | 5 | 5 | 5 | 5 | — | 5 |
| 181 | 5 | 5 | 5 | 5 | 5 | 5 | 5 | — | 5 | 5 | 5 | 5 | 5 |
| 234 | 5 | 5 | 5 | 5 | 5 | 5 | 5 | 5 | 5 | 5 | 5 | 5 | 5 |

[1]From Table 1 of Gracen and Grogan, 1974 (19)
[b]Fertility ratings:
1. Male sterile:
2. Sterile anthers exserted:
3. Partially fertile:
4. Slightly subnormal:
5. Fully fertile.

TABLE 2

Relative intensity of LBN dsRNA in 10 inbred backgrounds

| In-breds | Number of Crosses to Inbreds | | | | | | |
|---|---|---|---|---|---|---|---|
| | $F_1$ | $BC_1$ | $BC_2$ | $BC_3$ | $BC_4$ | $BC_5$ | $BC_6$ |
| 2123 | +++[a] | +++ | +++ | +++ | +++ | +++ | +++ |
| CO125 | ++ | + | + | + | + | + | + |
| NY327 | +++ | +++ | +++ | — | — | — | — |
| NY453 | +++ | +++ | — — | — — | | | |
| NY317 | +++ | ++ | — — | — — | | | |
| NY421 | +++ | — — | — — — | — — — | | | |
| 5125 | ++ | — | — — | — — — | — — — | — — — | |
| CO107 | + | — | — — | | | | |
| P39 | — | — | — | — — | — — | — — | |
| W37A | — | — — | — — | | | | |

[a]Scale in descending order from '+++', very prominent band, to '— — —', almost invisible band

TABLE 3

LBN cytoplasm inbred nucleus combinations available

| Genotype | Fertility Rating (1–5) |
|---|---|
| A638 | 1–3 |
| A554 | 1 |
| A641Ht | 1 |
| A661 | 1–3 |
| CQ210 | 1 |
| CQ177 | 1 |
| CQ214 | 1 |
| FR-22 | 1 |
| FR-23 | 1 |
| W64AHt | 1 |
| A632 | 1–3 |
| A634 | 1 |
| B75 | 1–3 |
| Pa83 | 1 |
| A664 | 1–3 |
| B85 | 1–3 |
| A665 | 1–3 |
| B14A | 5 |
| A239 | 3 |
| CO150 | 1 |
| NY821 | 3 |
| SD10 | 1 |
| CO113 | 3 |
| CO192 | 3 |
| H84 | 5 |
| Va20 | 3–4 |

What is claimed is:

1. A male sterile corn plant comprising:
    (a) a cytoplasm conferring the property of male sterility
    (b) an essentially homozygous genome and,
    (c) a double stranded RNA plasmid detectable either in plasmid profiles of said male sterile corn plant or detectable in plasmid profiles of a dsRNA test cross.
2. A male sterile corn plant as defined in claim 1 wherein said cytoplasm is LBN.
3. A male sterile corn plant as defined in claim 1 wherein said essentially homozygous genome is W182BN or 2132.
4. A male sterile corn plant as defined in claim 1 wherein said double stranded RNA plasmid is LBN1 or LBN2.
5. A male sterile corn plant comprising:
    (a) a cytoplasm conferring the property of male sterility and,
    (b) a double stranded RNA plasmid detectable either in plasmid profiles of said male sterile corn plant or detectable in plasmid profiles of dsRNA test cross.
6. A male sterile corn plant as defined in claim 5 wherein said cytoplasm is LBN.
7. A male sterile corn plant as defined in claim 5 wherein said double stranded RNA plasmid is LBN1 or LBN2.
8. A method for producing a hybrid corn seed comprising the steps of:
    (a) growing a cytoplasmic male sterile corn plant wherein said cytoplasmic male sterile corn plant contains and replicates therein a double stranded RNA plasmid detectable either in plasmid profiles of said cytoplasmic male sterile corn plant or detectable in plasmid profiles of a dsRNA test cross,
    (b) fertilizing the male sterile corn plant with pollen of a male fertile corn plant, and
    (c) harvesting a hybrid seed developed on said cytoplasmic male sterile corn plant.
9. A male sterile corn plant comprising a cytoplasm conferring the property of male sterility wherein said cytoplasm is LBN.

10. A method for producing hybrid corn seeds as defined in claim 8 wherein cells of said cytoplasmic male sterile corn plant contains an LBN-cytoplasm.

11. A method for producing a hybrid corn seed as defined in claim 8 wherein said double stranded RNA plasmid is LBN1 or LBN2.

12. A method for producing a hybrid corn seed as defined in claim 8 wherein said cytoplasmic male sterile corn plant is essentially genetically homozygous.

13. A method for producing a hybrid corn seed as defined in claim 8 wherein said cytoplasmic male sterile corn plant is genetically heterozygous.

14. A method for producing a hybrid corn seed as defined in claim 8 wherein said male fertile corn plant contains the restorer gene Rf3.

15. A method for producing a hybrid corn seed as defined in claim 8 wherein said male fertile corn plant contains the non-restorer gene Rf3.

* * * * *